United States Patent
Aboul-Hosn et al.

[11] Patent Number: 6,086,570
[45] Date of Patent: Jul. 11, 2000

[54] HEMOSTASIS VALVE WITH MEMBRANES HAVING OFFSET APERTURES

[75] Inventors: Walid N. Aboul-Hosn; Dale Scribner, both of Sacramento, Calif.

[73] Assignee: A-Med Systems, Inc., West Sacramento, Calif.

[21] Appl. No.: 09/163,103

[22] Filed: Sep. 29, 1998

[51] Int. Cl.$^7$ ................................. A61M 5/14
[52] U.S. Cl. .................. 604/256; 604/246; 604/167; 251/149
[58] Field of Search .................. 604/256, 415, 604/244, 246, 905, 167, 264; 251/149

[56] References Cited

U.S. PATENT DOCUMENTS

| | | | |
|---|---|---|---|
| 2,023,267 | 12/1935 | Rapt et al. | 128/141 |
| 3,067,425 | 12/1962 | Colley | 2/6 |
| 4,338,937 | 7/1982 | Lerman . | |
| 4,516,578 | 5/1985 | Shuffield . | |
| 4,626,245 | 12/1986 | Weinstein | 604/167 |
| 4,634,432 | 1/1987 | Kocak | 604/167 |
| 4,673,393 | 6/1987 | Suzuki et al. | 604/167 |
| 4,895,346 | 1/1990 | Steigerwald | 251/149.1 |
| 4,929,235 | 5/1990 | Merry et al. | 604/167 |
| 4,932,633 | 6/1990 | Johnson et al. | 251/149.1 |
| 5,000,745 | 3/1991 | Guest et al. | 604/256 |
| 5,007,900 | 4/1991 | Picha et al. . | |
| 5,041,095 | 8/1991 | Littrell | 604/167 |
| 5,102,395 | 4/1992 | Cheer et al. | 604/167 |
| 5,114,408 | 5/1992 | Fleischhaker et al. | 604/167 |
| 5,122,122 | 6/1992 | Allgood . | |
| 5,167,637 | 12/1992 | Okada et al. | 604/167 |
| 5,234,408 | 8/1993 | Griffith . | |
| 5,234,455 | 8/1993 | Mulhollan . | |
| 5,267,960 | 12/1993 | Hayman et al. . | |
| 5,290,249 | 3/1994 | Foster et al. . | |
| 5,358,488 | 10/1994 | Suriyapa . | |
| 5,387,196 | 2/1995 | Green et al. . | |
| 5,391,156 | 2/1995 | Hildwein et al. . | |
| 5,549,565 | 8/1996 | Ryan et al. . | |
| 5,618,270 | 4/1997 | Orejola . | |
| 5,643,227 | 7/1997 | Stevens | 604/264 |
| 5,649,953 | 7/1997 | Lefebvre . | |
| 5,683,378 | 11/1997 | Christy . | |
| 5,741,234 | 4/1998 | Aboul-Hosn . | |
| 5,755,697 | 5/1998 | Jones et al. . | |

Primary Examiner—Corrine McDermott
Assistant Examiner—Cris L. Rodriguez
Attorney, Agent, or Firm—Jonathan D. Spangler

[57] ABSTRACT

A self-sealing hemostasis valve having a first membrane with an opening offset from the center and a second membrane with an opening offset from the center in a direction opposite of the offset in the first membrane. The two membranes are joined about their outer edges. Access through the two elastomeric membranes without tearing is available at the intersection of the openings in the membrane assembly when the two membranes are deformed by an instrument being inserted through the hemostasis valve.

8 Claims, 4 Drawing Sheets

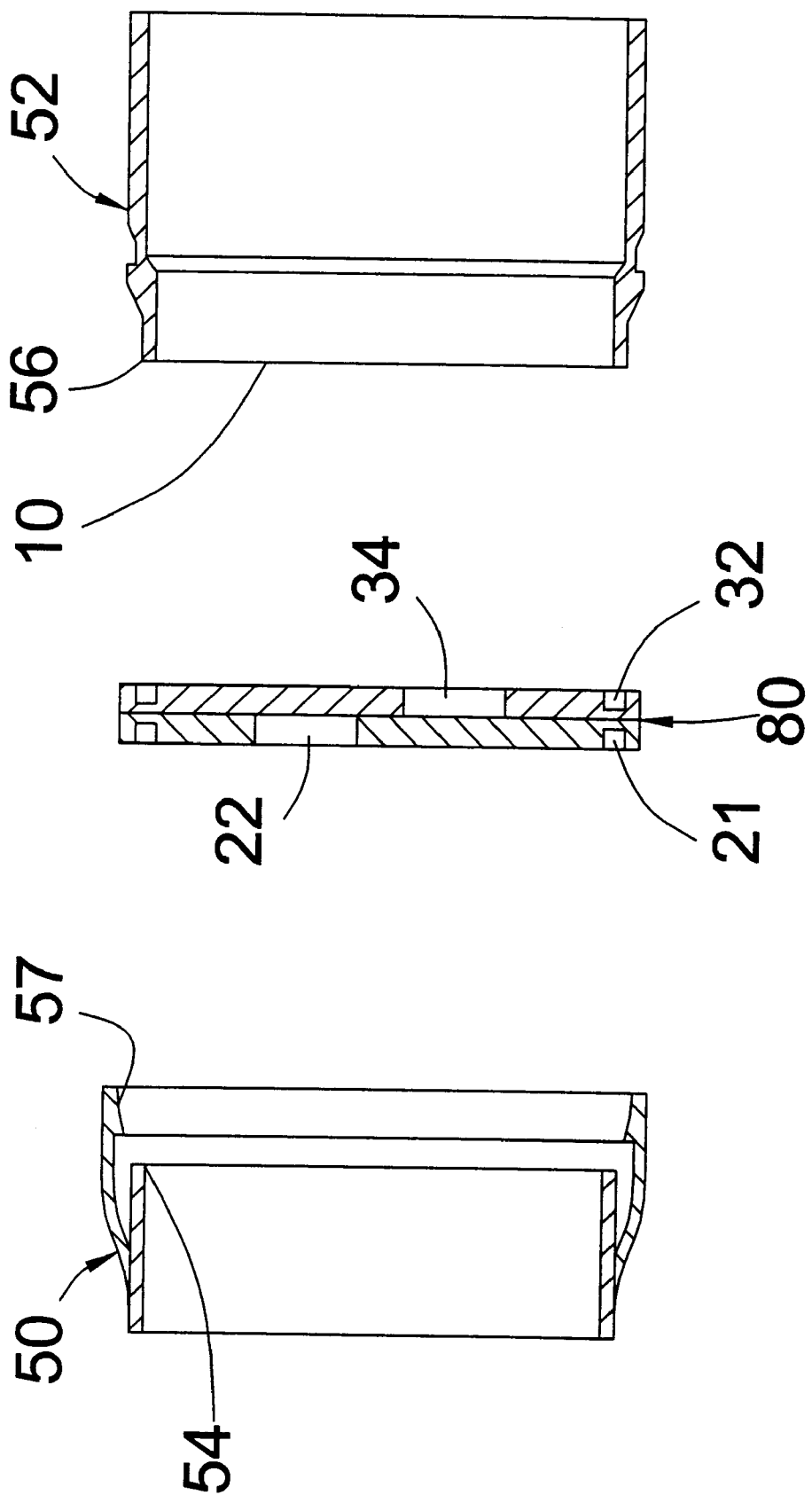

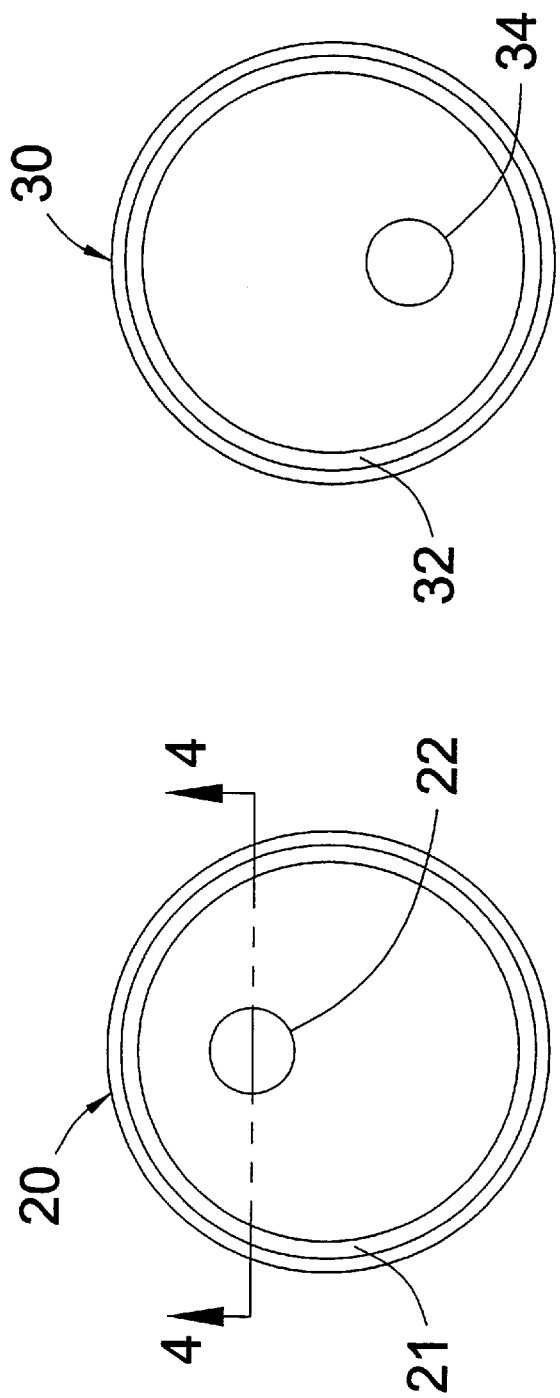
Figure 3
Figure 2
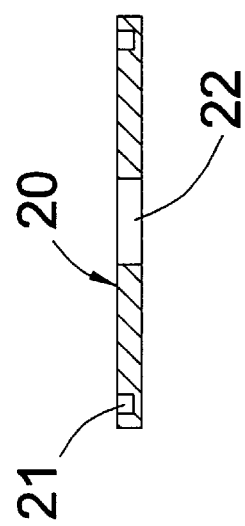
Figure 4

HEMOSTASIS VALVE WITH MEMBRANES HAVING OFFSET APERTURES

FIELD OF THE INVENTION

This invention relates to hemostasis valves that prevent blood loss when a guidewire, cannula or other surgical instrument is removed or inserted through the hemostasis valve.

BACKGROUND OF THE INVENTION

During surgical procedures it is desirable to insert many different instruments within a patient's body cavity, vessel or other location. In minimally invasive surgical procedures, many different instruments must be introduced through surgical ports within the patient's body. Hemostasis valves are used to form seals around the instruments that are introduced into the patient's body.

Hemostasis valves may also be employed on cannulas or catheters that are deployed within the patient during surgical procedures. A catheter with a hemostasis valve located within a first lumen may be deployed within a patient's vessel, heart or other body cavity then a second catheter or guidewire may be deployed through the lumen of the first catheter, passing through the hemostasis valve which provides a fluid tight seal between the two instruments. The benefit of doing so allows the surgeon to make a single incision rather than multiple incisions to insert cannulas or other surgical devices within the patient.

There is a need for improvement of the hemostasis valve, so that an individual valve is capable of accommodating a variety of different sized catheters or other objects penetrating it without leaking or becoming damaged. Further, it is preferred that the structure of the valve be inexpensive and easy to manufacture.

SUMMARY OF THE INVENTION

The present invention is a self-sealing hemostasis valve having a first membrane with an opening offset from the center and a second membrane with an opening offset from the center in a direction opposite of the offset in the first membrane. The two membranes are joined about their outer edges. Access through the two elastomeric membranes without tearing is available at the intersection of the openings in the membrane assembly when the two membranes are deformed by an instrument being inserted through the hemostasis valve. Each of the openings in the membranes stretch accordingly to accommodate surgical instruments of various diameters and shapes.

BRIEF DESCRIPTION OF THE DRAWINGS

The advantages of the present invention will become more fully apparent from the following detailed description when read in conjunction with the accompanying drawings with like reference numerals indicating corresponding parts throughout.

FIG. 1 is an exploded cross-sectional view of a hemostasis valve in accordance with the present invention.

FIG. 2 is a front view of one membrane of the membrane assembly.

FIG. 3 is a rear view of the second membrane in the membrane assembly.

FIG. 4 is a cross-sectional view taken along line 4—4 of FIG. 2.

DETAILED DESCRIPTION OF THE PREFERRED EMBODIMENT

Figure 5:
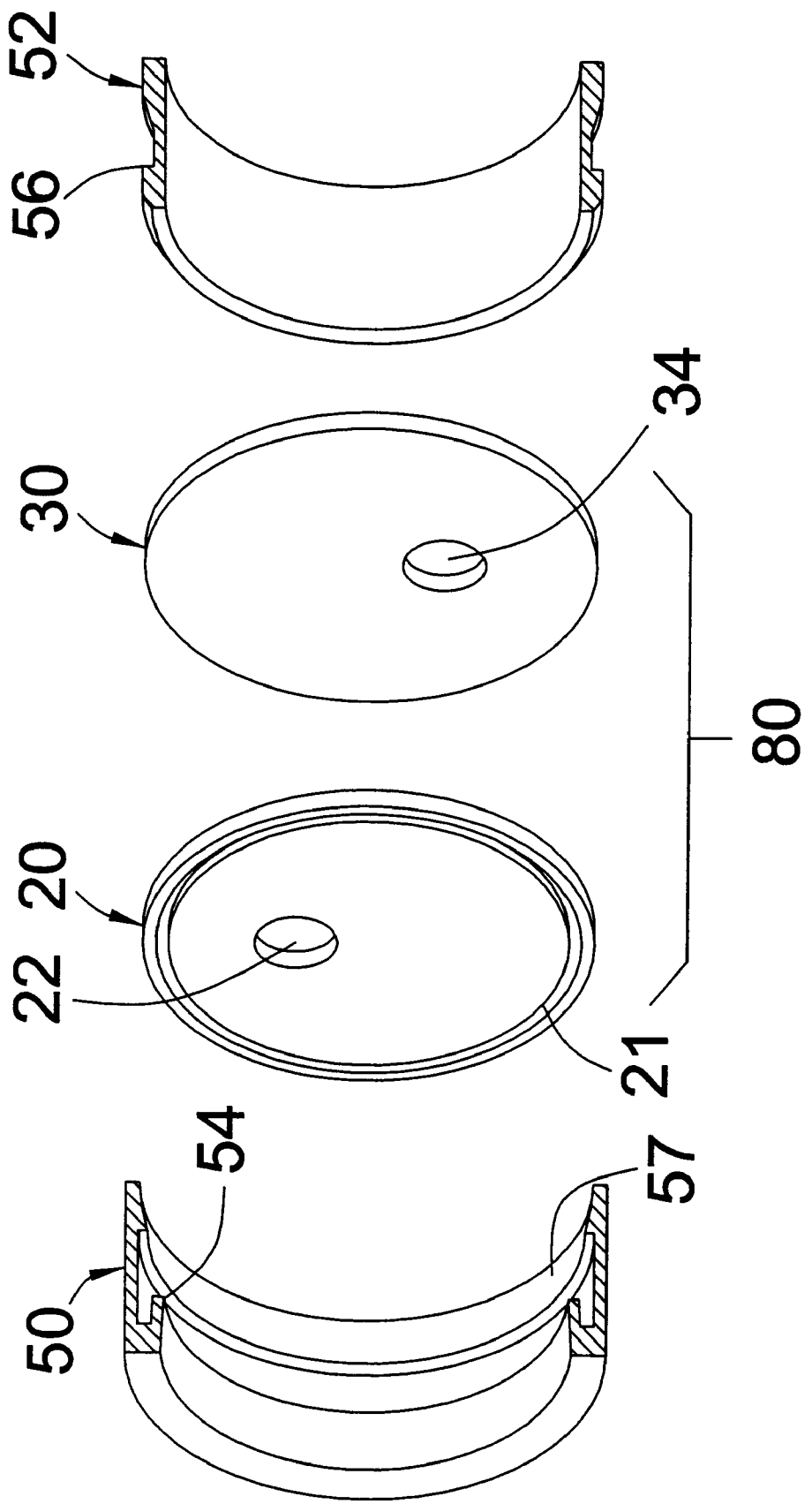
FIG. 5 is an exploded, partial cross-sectional view of the hemostasis valve.

Referring to FIG. 1, housing 10 is adapted to be attached to a medical instrument such as a cannula. Housing 10 comprises generally cylindrical body 52 and cap 50 which houses membrane assembly 80. The membranes of membrane assembly 80 are formed of an elastomeric material such as silicone or any other similar material known to one skilled in the art.

As seen best in FIGS. 2, 3, 5 and 6, membrane assembly 80 is formed of two generally circular shaped flexible membrane discs 20 and 30. First membrane 20 has an opening 22 which is disposed offset from but adjacent to the center of the membrane. Second membrane 30 has an opening 34 which is disposed offset in the opposite direction from but adjacent to the center of the membrane. The opening 34 in the second membrane is a mirror image about a line through the center of the membrane of opening 22 located within the first membrane 20. First membrane 20 and second membrane 30 are joined at their edges with a biocompatible adhesive thereby forming a single membrane assembly 80. Other attachment may be utilized to join the separate layers together such as staples, heat sealing, etc. When assembled to form membrane assembly 80, the axis of opening 22 is not coaxial with the axis of opening 34, thereby a portion of each membrane overlays the opening in the opposite membrane forming a seal over each opening. Opening 21 in first membrane 20 is occluded by second membrane 30 and opening 34 in second membrane 30 is occluded by first membrane 20.

Access through the two elastomeric membranes 20 and 30 without tearing is available at the intersection of the openings 22 and 34 in the membrane assembly 80 when the two membranes are deformed by an instrument being inserted through the hemostasis valve. As the membranes are stretched distally during insertion of an instrument therethrough, the openings 22, 34 become aligned to allow passage of the instrument therethrough while providing a tight seal around the instrument. Each of the openings in the membranes 20, 30 stretch accordingly to accommodate surgical instruments of various diameters and shapes.

Figure 6:
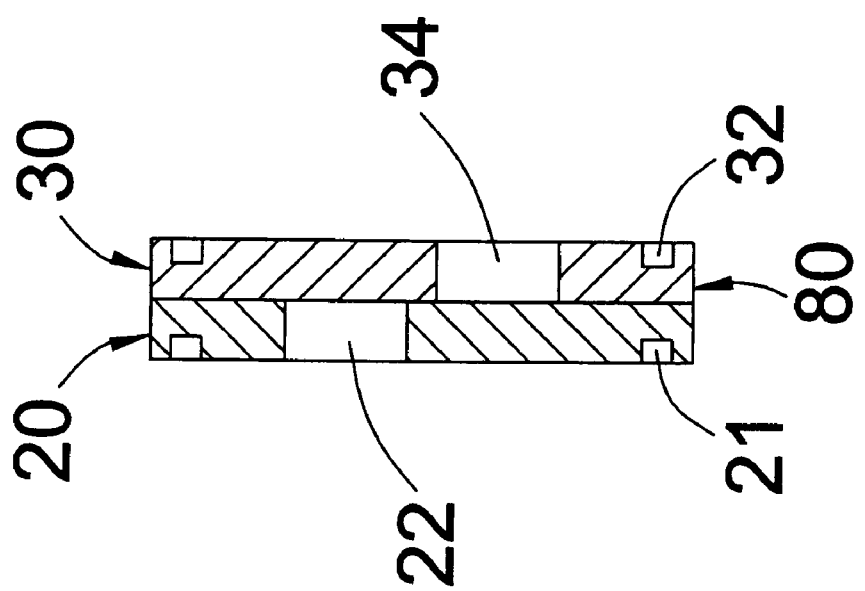
FIG. 6 is a cross-sectional view of the membrane assembly.

The membrane assembly 80 is placed within the housing 10 such that annular channels 21 and 32 about the circumference of the membranes engage the housing. The housing 10 includes an end cap 50 which attaches to main body 52 having members 54 for securing the membrane assembly 80 in the housing. The end cap 50 can be shaped to define an aperture in which a medical instrument may be inserted. As best seen in FIG. 6, membrane assembly 80 contains channels 21 and 32. Channel 32 is placed about the proximal end of body 52. Cap 50 member 54, other disposed radially thereabout. Cap 50 contains extensions 57 for locking to body 52 thereby forming housing 10 containing membrane assembly 80.

Preferably, the elastomeric material used for each of the membranes is a medically compatible material which seals well, for example natural rubber, latex, silicone or any other appropriate material apparent to one skilled in the art. As described, the membrane assembly that comprises the sealing barrier may be carried within a housing. It is within the scope of the invention that the membrane assembly may be positioned at the end of a cannula or catheter for medical use, though other uses of the hemostasis valve are contemplated to be within the scope of this invention.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiments disclosed, but that the invention will include all embodiments falling within the scope of the appended claims.

What is claimed is:

1. A hemostasis valve comprising:
    a housing having a main body and a cap member, said main body and said cap member each having a generally annular membrane engagement member and an internally disposed lumen adapted to pass a surgical instrument therethrough; and
    a sealing membrane assembly adapted to be received within said housing to maintain hemostasis during the passage of a surgical instrument through said housing and into a body cavity of a patient, wherein said sealing membrane assembly includes a first membrane and a second membrane, each of said first and second membranes having an aperture formed therethrough adapted to pass a surgical instrument therethrough, said apertures of said first and second membranes being offset axially, and wherein each of said first and second membranes include an annular channel adapted to receive said membrane engagement members to form a seal between the sealing membrane assembly and said housing.

2. The hemostasis valve of claim 1 wherein said first membrane and said second membrane are joined at their outer edges.

3. The hemostasis valve of claim 1, wherein said aperture in said first membrane is offset from a center of said first membrane.

4. The hemostasis valve of claim 3, wherein said second membrane is substantially a mirror image of said first membrane.

5. A hemostasis valve comprising:
    a housing having a first generally annularly extending membrane engagement member disposed a distance apart from, and in generally co-aligned fashion with, a second generally annularly extending membrane engagement member; and
    a sealing membrane assembly having first and second membranes positioned adjacent one another, said first membrane having a first annular channel formed therein, said second membrane having a second annular channel formed therein, said first and second annular channels being adapted to receive and engage with said first and second membrane engagement member to said sealing membrane assembly within said housing;
    said first membrane having a first opening;
    said second membrane having a second opening disposed offset from said first opening, said first and second openings being adapted to form a hemostatic seal about a surgical instrument when said surgical instrument is passed through said first and second membranes for insertion into a body cavity of a patient.

6. The hemostasis valve of claim 6, wherein the first and second openings are circular.

7. The hemostasis valve of claim 5, wherein said housing includes a cap member and a main body member, said first generally annularly extending membrane engagement member forming part of said cap member, and said second generally annularly extending membrane engagement member forming part of said main body member.

8. A hemostasis valve, comprising:
    a hemostatic sealing assembly including a first sealing membrane and a second sealing membrane, said first sealing membrane having an aperture formed therethrough and a generally annular channel formed therein, said second sealing membrane having an aperture disposed offset from said aperture formed through said first sealing membrane and a generally annular channel formed therein; and
    a housing assembly including a first membrane engagement member and a second membrane engagement member, said first and second membrane engagement members extending in a generally annularly fashion towards one another to be received within said annular channels of said first and second sealing members to thereby maintain said hemostatic sealing assembly within said housing assembly;
    said apertures formed in said first and second sealing membranes serving to establish a hemostatic seal around a surgical instrument passing through said hemostatic sealing assembly for insertion into a body cavity of a patient.

* * * * *